(12) United States Patent
Keitmann et al.

(10) Patent No.: US 6,320,081 B1
(45) Date of Patent: Nov. 20, 2001

(54) O-NITRO(THIO)PHENOL DERIVATIVES, AND THEIR PREPARATION

(75) Inventors: Michael Keitmann, Weisendorf; Recai Sezi, Röttenbach; Andreas Weber, Ursensollen, all of (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 09/161,149

(22) Filed: Sep. 24, 1998

(30) Foreign Application Priority Data

Sep. 24, 1997 (DE) ................................. 197 42 135

(51) Int. Cl.⁷ .................. C07C 321/24; C07C 39/00; C07C 43/20
(52) U.S. Cl. .............. 568/44; 568/631; 568/45; 568/50
(58) Field of Search ................. 568/44, 45, 51, 568/53, 55, 61, 62, 67, 631, 650, 716, 717

(56) References Cited

U.S. PATENT DOCUMENTS

| 2,385,282 | 9/1945 | Jaeger, Jr. . |
| 3,350,459 | 10/1967 | Pelster et al. . |
| 3,947,434 | 3/1976 | Spencer et al. . |
| 4,310,527 | 1/1982 | Jaeggi et al. . |
| 4,419,122 | * 12/1983 | Swithenbank ............ 504/198 |
| 5,503,640 | 4/1996 | Junino et al. . |

FOREIGN PATENT DOCUMENTS

| 1 178 440 | 9/1964 | (DE) . |
| 0317942 | 5/1989 | (EP) . |
| 0264678 | 9/1991 | (EP) . |
| 0300326 | 6/1993 | (EP) . |
| 1205518 | 9/1986 | (SU) . |

OTHER PUBLICATIONS

Chemical Abstracts No. XP–002087377, vol. 72 (1970), May 25 No. 21, p. 399.
International Application WO 97/23216 (Bigge et al.), dated Jul. 3, 1997.
Jules Freedman et al.: "The Preparation of 3,4–Dihydro–1–benzoxepin–5(2H)–ones", J. Heterocyclic Chem., 26, 1547 (1989), pp. 1547–1553.
CA:116:209649 abs of Toxicol Environ Chem by Brodskii E, 34 (2–4) pp 105–112, 1992.*
CA:123:169595 abs of JP06293640, Feb. 1994.*
CA:87:189338 abs of Planta Med By Glombitza 32(1) pp 33–45, 1977.*
CA:95:220393 abs of Acta Polym 32 (8) by Mikitaev pp 435–460, 1981.*
CA:99:175374 abs of EP83204, Jul. 1983.*
CA:74:111715 abs Of J Chem Soc C (3) pp 562–566, 1971.*
Journal of Med. Chem. vol. 8 by Augstein pp 446–454, 1965.*
CA:129:275910 abs of WO 9842680, Oct. 1998.*
CA:92:181056 abs of Khim. Geterotsikl. Soedin. (12) pp 1620–1623 by Korshak, 1979.*

* cited by examiner

Primary Examiner—Jean F. Vollano
(74) Attorney, Agent, or Firm—Herbert L. Lerner; Laurence A. Greenberg; Werner H. Stemer

(57) ABSTRACT

The invention relates to novel o-nitrophenol derivatives and o-nitrothiophenol derivatives of the following structure:

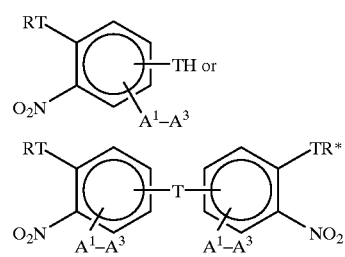

where:
$A^1$ to $A^3$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$; T is O or S; R is an aliphatic or araliphatic radical; and R* is H or R.

13 Claims, No Drawings

O-NITRO(THIO)PHENOL DERIVATIVES, AND THEIR PREPARATION

BACKGROUND OF THE INVENTION

Field of the Invention

The invention relates to novel o-nitrophenol derivatives and o-nitrothiophenol derivatives, which are also jointly abbreviated to o-nitro(thio)phenol derivatives, and to a process for their preparation.

The preparation of high-temperature-stable polymers, such as polybenzoxazoles (PBOs) and their precursors, and the preparation of hydroxypolyimides requires bis-o-aminophenols (in this respect, see, for example, EP 0 264 678 B1 and EP 0 300 326 B1). These monomers can be prepared by reducing the corresponding bis-o-nitrophenols (in this respect, see EP 0 317 942 A2, SU 1 205 518 A and "Polymer Preprints" 34(1), 1993, pages 425 and 426).

Bis-o-nitrophenols can be prepared by nitrating bisphenols. However, this gives isomers and also polynitro compounds, which is very disadvantageous since, if the nitration is not complete, i.e. to 100%, and does not take place entirely isomer-free, i.e. nitration only taking place in the o-position to the hydroxyl group, then the reduction is in some cases followed by the formation of aminophenols which do not allow complete cyclization in the PBO precursor and considerably impair the properties of the polybenzoxazole.

It is also already known to prepare nitrophenol derivatives, i.e. bis(o-benzyloxynitrophenyl) compounds, for said purpose. This is achieved by nucleophilic substitution (see "Polymer Preprints", in loco citato). However, this process requires high temperatures, namely significantly higher temperatures than 100° C. (solutions in dimethylacetamide/toluene are refluxed). However, high reaction temperatures promote side-reactions, which reduce the yield (it is a maximum of 73%) and make purification of the target product more difficult. In addition, the bis-o-aminophenols prepared in this way are not stable to oxidation.

In general, there is a lack of suitable aminophenols—and correspondingly also of nitrophenols—for the preparation of polymers which satisfy the greatly increased demands of microelectronics. In addition, the type of aminophenol employed has a strong effect on the property profile of the PBO precursor or polybenzoxazole prepared therewith. For example, not only the thermal, electrical and mechanical behavior, but also the solubility and hydrolysis stability and numerous other properties of the polymer are greatly affected by the monomer used in the preparation.

SUMMARY OF THE INVENTION

The object of the invention is to provide o-nitrophenol derivatives and o-nitrothiophenol derivatives which are suitable for the preparation of selected o-aminophenols or o-aminothiophenols of high isomer purity and stability to oxidation which serve as particularly suitable monomers for the preparation of polymer precursors.

This is achieved in accordance with the invention by o-nitrophenol derivatives and o-nitrothiophenol derivatives of the following structure:

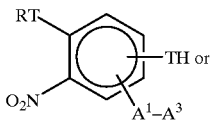

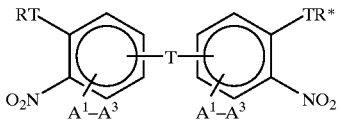

in which
$A^1 A^3$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$;
T=O or S;
R=alkyl, alkoxyalkyl, alkenyl, alkoxyalkenyl, alkynyl or alkoxyalkynyl, each having a maximum of 6 carbon atoms, phenyl, phenacyl or benzyl, and benzylalkyl, benzylalkenyl, benzyloxyalkyl, benzyloxyalkenyl, benzylalkoxyalkyl or benzylalkoxyalkenyl, each having a maximum of four aliphatic carbon atoms;
R*=H or R;
provided that, in the o-nitro(thio)phenol derivative (1), R cannot be alkyl if $A^1$ is an F-atom in the m-position to the $NO_2$ group, $A^2$ and A3 are H, and the TH group is in the o-position to the $NO_2$ group.

The characterization "$A^1$–$A^3$" in the structural formulae means that the nitrophenyl groups contain radicals $A^1$, $A^2$ and $A^3$. In (2), the corresponding radicals in the two nitrophenyl groups may be identical or different.

The o-amino(thio)phenols which can be prepared from the o-nitro(thio)phenol derivatives of the invention result in polymer precursors which, after cyclization, give polybenzoxazoles or polybenzothiazoles which have low moisture absorption, high temperature stability and a high degree of planarization. The polymer precursors are readily soluble in many organic solvents, such as acetone, cyclohexanone, ethyl lactate, diethylene glycol mono- and diethyl ether, N-methylpyrrolidone and γ-butyrolactone, and in aqueous-alkaline developers containing no metal ions. They are therefore highly suitable as base polymers for dielectrics which can be photostructured positively and can be developed in aqueous-alkaline media. The precursors can easily be applied to substrates, such as silicon wafers, by spin-coating methods, they form uniform films, and can readily be cyclized on the substrate.

The o-nitro(thio)phenol derivatives of the formula (1) can be prepared by selectively removing the radical $R^2$ from a compound of the structure

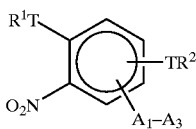

and replacing it by H at a temperature of from 20 to 100° C., whereby
(a) for $R^1$=alkyl, alkoxyalkyl, alkenyl, alkoxyalkenyl, alkynyl or alkoxyalkynyl (each having a maximum of 6 carbon atoms) and $R^2$=phenyl, phenacyl or benzyl, and benzylalkyl, benzylalkenyl, benzyloxyalkyl, benzyloxyalkenyl, benzylalkoxyalkyl or benzylalkoxyalkenyl (each having a maximum of four aliphatic carbon atoms), the removal of $R^2$ is carried out using trifluoroacetic acid, p-toluenesulfonic acid, lithium tert-butoxide, sodium tert-butoxide, potassium tert-butoxide, lithium aluminum hydride, sodium aluminum hydride or potassium aluminum hydride, or by hydrogenation using hydrogen on Pd/C;

(b) for $R^1$=phenyl, phenacyl or benzyl, and benzylalkyl, benzylalkenyl, benzyloxyalkyl, benzyloxyalkenyl, benzylalkoxyalkyl or benzylalkoxyalkenyl (each having a maximum of four aliphatic carbon atoms), and $R^2$=alkyl, alkoxyalkyl, alkenyl, alkoxyalkenyl, alkynyl or alkoxyalkynyl (each having a maximum of 6 carbon atoms), the removal of $R^2$ is carried out using a metal or a metal compound in a protic solvent.

The nitro compound of the structure shown above can be prepared from the corresponding dihalogen compound (X in place of $R^1T$ and $R^2T$) by reaction with compounds $R^1TH$ and $R^2TH$, for example allyl alcohol and benzyl alcohol, or with corresponding alkali metal salts.

Alternatively, o-nitro(thio)phenol derivatives of structure (1) can be prepared by reacting a compound of the structure

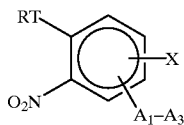

where R is as defined above and X is halogen, with an excess of a basic agent TH⁻ (where T=O or S) at a temperature of from 20 to 100° C.

If the basic agent is not employed in excess, but in a stoichiometric amount, this results—under otherwise identical conditions—in an o-nitro(thio)phenol derivative of structure (2) where R*=R. In order to prepare compounds in which the two nitrophenyl groups contain different radicals $A^1$ to $A^3$, correspondingly different halogen-containing nitro compounds are employed.

o-Nitro(thio)phenol derivatives of the structure (2) where R*=H are prepared by reacting an o-nitro(thio)phenol derivative of structure (1) with a compound of the structure

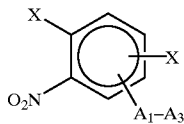

where X is halogen,
and then replacing the halogen X in the o-position to the $NO_2$ group by TH by reaction with an excess of a basic agent TH⁻ (where T=O or S) at a temperature of from 20 to 100° C.

DESCRIPTION OF PREFERRED EMBODIMENTS

The radicals $R^1$ and $R^2$ preferably have the following meanings: methyl, ethyl, isopropyl, allyl or methoxymethyl, and phenyl, phenacyl (i.e. $C_6H_5$—CO—$CH_2$—), benzyl or benzyloxymethyl.

The metals employed for the selective removal of $R^2$ are preferably Ni, Se, Rh, Pd, Pt and Hg, and the metal compounds can be salts, organometallic compounds or complex compounds, such as $(CH_3COO)_2Pd(C_6H_5)_3$. The removal is advantageously carried out using Pd/C (palladium/carbon), $SeO_2$ or HgCl.

The basic agent acts as a source of the anion TH⁻ and can be an alkali metal hydroxide, carbonate, or hydrogen carbonate; an alkaline earth metal hydroxide; an aqueous solution of a tertiary or quaternary nitrogen base, such as tetramethylammonium hydroxide; or an aqueous solution of an alkali hydrogen sulfide, such as sodium hydrogen sulfide.

The reactions are generally carried out in a solvent. Examples of suitable solvents are dimethylformamide, dimethylacetamide, dimethyl sulfoxide, N-methylpyrrolidone and γ-butyrolactone. The o-nitro(thio)phenol derivatives are obtained in a yield of ≧85%.

The preparation of bis-o-amino(thio)phenols from the o-nitro(thio)phenol derivatives of the invention is described in the simultaneously filed German Patent Application No. 197 42 196.2—"Bis-o-amino(thio)phenols, and their preparation" (GR 97 P 3684).

The o-nitro(thio)phenol derivatives of the invention are also suitable for the preparation of o-amino(thio) phenolcarboxylic acids, which are likewise used for the preparation of polybenzoxazoles and polybenzothiazoles or the corresponding polymer precursors. The preparation of o-amino-(thio)phenolcarboxylic acids is described in the simultaneously filed German Patent Application No. 197 42 194.6—"o-Amino(thio)phenolcarboxylic acids, and their preparation" (GR 97 P 3689).

The invention will be illustrated in greater detail below with reference to working examples.

EXAMPLE 1

Preparation of 2-benzyloxy-4-fluoronitrobenzene (5-fluoro-2-nitrophenyl benzyl ether)

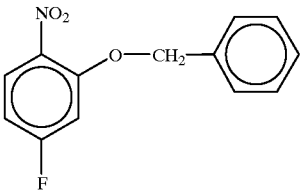

31.4 g of 5-fluoro-2-nitrophenol (0.2 mol) and 34.3 g of benzyl bromide (0.2 mol) are dissolved in 200 ml of dry acetonitrile in a 500 ml three-neck flask fitted with reflux condenser, stirrer and nitrogen inlet. 60 g of potassium carbonate (0.43 mol) are added, and the solution is refluxed for 2 hours in a temperature-controllable oil bath. The reaction solution is then allowed to cool to room temperature, and the residue is filtered off via a fluted filter. The resultant solution is then evaporated to half in a rotary evaporator and left to stand overnight at room temperature, during which the yellow-orange reaction product precipitates in crystalline form. The reaction product is then filtered off via a fluted filter, recrystallized from ethanol and then dried for 48 hours under nitrogen at 40° C./10 mbar in a vacuum drying cabinet.

Characterization

Mass spectrum: molecular peak at 247

Elemental analysis: Theoretical value (in %) : C: 63.2 H: 4.1 N: 5.7. Found (in %) : C: 62.9 H: 3.9 N: 5.8.

m.p.:55° C.

EXAMPLE 2

Preparation of 2-benzyloxy-4-hydroxynitrobenzene

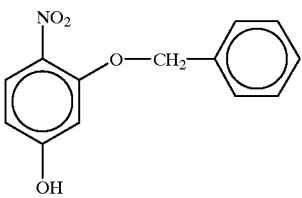

39.5 g of the 2-benzyloxy-4-fluoronitrobenzene (0.16 mol) prepared as described in Example 1 are added to a mixture of an aqueous potassium hydroxide solution prepared from 27.2 g of potassium hydroxide (0.48 mol) and 180 ml of distilled water, and 150 ml of dimethyl sulfoxide in a three-neck flask fitted with reflux condenser, stirrer and nitrogen inlet, and the mixture is then heated to 100° C. After 4 hours, the reaction solution is allowed to cool to room temperature, and the residue is filtered off via a fluted filter. The dark-orange solution is then added to 800 ml of water, and concentrated hydrochloric acid is added with vigorous stirring until the mixture is acidic. Within about 1 hour, a white-yellowish, flaky reaction product precipitates; this is filtered off via a Büchner funnel and washed three times with water. The reaction product is recrystallized from ethanol and then dried for 48 hours under nitrogen at 40 ° C./10 mbar in a vacuum drying cabinet.

Characterization

Mass spectrum: molecular peak at 245

Elemental analysis: Theoretical value (in %) : C: 63.7 H: 4.5 N: 5.7. Found (in %) : C: 63.4 H: 4.4 N: 5.9.

m.p.: 117° C.

EXAMPLE 3

Preparation of the potassium salt of 2-benzyloxy-4-hydroxynitrobenzene

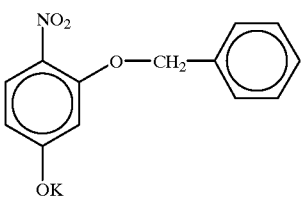

40 g of the 2-benzyloxy-4-hydroxynitrobenzene prepared as described in Example 2 (0.163 mol) are dissolved in 300 ml of tetrahydrofuran in a three-neck flask fitted with reflux condenser, stirrer and nitrogen inlet. 19.2 g of potassium tert-butoxide (0.171 mol) are added in portions to the solution at room temperature with vigorous stirring. A highly exothermic reaction commences, during which the potassium salt precipitates. 15 minutes after addition of potassium tert-butoxide, the mixture is refluxed for a further 1 hour to complete the reaction. The mixture is then allowed to cool to room temperature, and the reaction product is filtered off via a Büuchner funnel and rinsed three times with a mixture of tetrahydrofuran and petrol ether (volume ratio 1:1). The reaction product is then dried for 48 hours under nitrogen at 40° C./10 mbar in a vacuum drying cabinet.

Characterization:

Mass spectrum: molecular peak at 283

Elemental analysis: Theoretical value (in %) : C: 55.1 H: 3.6 N: 4.9. Found (in %) : C: 55.3 H: 3.7 N: 4.8.

EXAMPLE 4

Preparation of 1-benzyloxy-4-nitro-2,3,5,6-tetrafluorobenzene

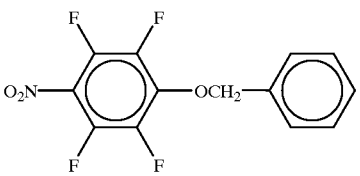

21.3g of pentafluoronitrobenzene (0.1 mol) and 12 g of benzyl alcohol (0.11 mol, i.e. a 10% excess) are dissolved in 200 ml of dry γ-butyrolactone in a three-neck flask fitted with stirrer. 30 g of potassium carbonate (0.22 mol) are then added in portions, and the mixture is stirred at room temperature for 24 hours. The reaction solution is then filtered via a fluted filter, and the crude product is extracted by shaking with 200 ml of ethyl acetate and 300 ml of water. The organic phase is washed three times with water, dried over sodium sulfate and evaporated to half in a rotary evaporator. The reaction product crystallizes from the initially viscous solution. The precipitated reaction product is then recrystallized from a mixture of methylene chloride and petrol ether (volume ratio 1:1) and then dried for 48 hours under nitrogen at 40° C./10 mbar in a vacuum drying cabinet.

Characterization:

Mass spectrum: molecular peak at 301

Elemental analysis: Theoretical value (in %) : C: 51.8 H: 2.3 N: 4.7. Found (in %) : C: 51.8 H: 2.3 N: 4.7.

EXAMPLE 5

Preparation of 1-benzyloxy-3-(prop-2-enyloxy)-4-nitro-2,5,6-trifluorobenzene

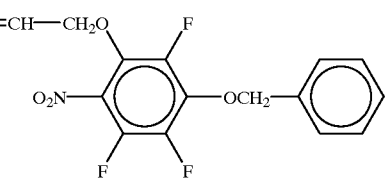

30.1 g of the 1-benzyloxy-4-nitro-2,3,5,6-tetrafluorobenzene prepared as described in Example 4 (0.1 mol) are dissolved in 250 ml of dry acetonitrile in a three-neck flask fitted with reflux condenser and stirrer, and 8 g of sodium prop-2-enolate (0.1 mol) are added in portions to the solution. The reaction mixture is stirred at room temperature for 1 hour and then refluxed for 24 hours. The reaction solution is then filtered via a fluted filter, and the crude product is extracted by shaking with 150 ml of ethyl acetate and 300 ml of water. The organic phase is washed three times with water, dried over sodium sulfate and evaporated to half in a rotary evaporator. The precipitated reaction product is then recrystallized from a mixture of n-hexane and methylene chloride (volume ratio 1:1) and then dried for 48 hours under nitrogen at 40° C./10 mbar in a vacuum drying cabinet.

Characterization:

Mass spectrum: molecular peak at 339

Elemental analysis: Theoretical value (in %) : C: 56.6 H: 3.6 N: 4.1. Found (in %) : C: 56.5 H: 3.5 N: 4.2.

EXAMPLE 6

Preparation of 3-(prop-2-enyloxy)-4-nitro-2,5,6-trifluorophenol

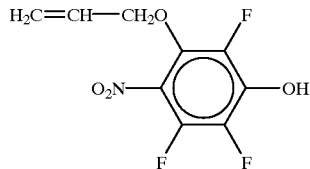

33.9 g of the 1-benzyloxy-3-(prop-2-enyloxy)-4-nitro-2,5,6-trifluorobenzene prepared as described in Example 5 (0.1 mol) are dissolved in 120 ml of trifluoroacetic acid in a three-neck flask fitted with reflux condenser and stirrer, and the mixture is then refluxed for 4 hours. The reaction solution is then allowed to cool to room temperature, and the crude product is extracted by shaking with 200 ml of ethyl acetate and 300 ml of water. The organic phase is washed three times with water, dried over sodium sulfate and evaporated to half in a rotary evaporator. The precipitated reaction product is then recrystallized from a mixture of n-hexane and methylene chloride (volume ratio 1:1) and then dried for 48 hours under nitrogen at 40° C./10 mbar in a vacuum drying cabinet.

Characterization:

Mass spectrum: molecular peak at 249

Elemental analysis; Theoretical value (in %) : C: 43.4 H: 2.4 N: 5.6. Found (in %) : C: 43.3 H: 2.5 N: 5.6.

EXAMPLE 7

Preparation of bis(3-benzyloxy-4-nitrophenyl) ether

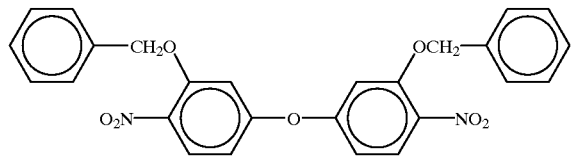

400 g of dimethyl sulfoxide and a solution of 37 g of potassium hydroxide (0.66 mol) in 400 ml of water are warmed to 100° C. in a three-neck flask fitted with reflux condenser and stirrer. 163 g of the 5-fluoro-2-nitrophenyl benzyl ether prepared as described in Example 1 (0.66 mol) are then added in portions, and the mixture is then heated at 100° C. for 8 hours. After the mixture has been cooled to room temperature, a colorless reaction product precipitates; this is filtered off, washed with water and dried. The reaction product is then recrystallized from ethyl acetate.

Characterization:

Mass spectrum: molecular peak at 472 m.p.: 119° C.

EXAMPLE 8

Preparation of bis(4-amino-3-hydroxyphenyl) ether

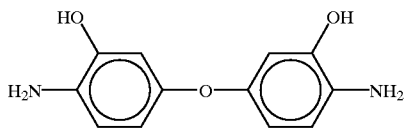

In this example, all steps are carried out under a protective gas using degassed solvent. 23.6 g of bis(3-benzyloxy-4-nitrophenyl) ether prepared as described in Example 7 (0.05 mol) are dissolved in 200 ml of tetrahydrofuran, and 2.36 g of Pd/C (palladium/carbon) are added to the solution. The mixture is then hydrogenated at room temperature in an autoclave using hydrogen at a pressure of 2 bar. The resultant mixture is filtered, and about two-thirds of the solvent is distilled off; during this, a colorless product begins to precipitate. This product is filtered off with suction, washed with cold tetrahydrofuran and dried under reduced pressure. A second crystal fraction can be recovered from the mother liquor by further evaporation.

| Characterization: | |
|---|---|
| Mass spectrum: | molecular peak at 232 |
| Elemental analysis: | |
| Theoretical value (in %): | C: 62.1    H: 5.2    N: 12.1 |
| Found (in %): | C: 61.8    H: 5.4    N: 12.1 |
| m.p.: | 209° C. |

EXAMPLE 9

Preparation of 1-(4-nitro-2,3,5,6-tetrafluorophenoxy)-3-(prop-2-enyloxy)-4-nitro-2,5,6-trifluorobenzene

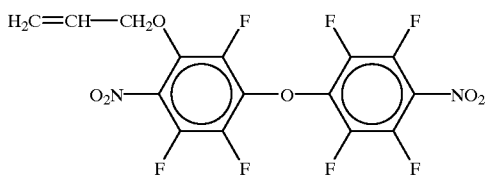

24.9 g of 3-(prop-2-enyloxy)-4-nitro-2,5,6-trifluorophenol prepared as described in Example 6 (0.1 mol) and 21.3 g of pentafluoronitrobenzene (0.1 mol) are dissolved in 300 ml of γ-butyrolactone in a three-neck flask fitted with stirrer. 30 g of potassium carbonate (0.22 mol) are then added in portions, and the mixture is stirred at room temperature for 24 hours. The reaction solution is then filtered via a fluted filter, and the crude product is extracted by shaking with 200 ml of ethyl acetate and 300 ml of water. The organic phase is washed three times with water, dried over sodium sulfate and evaporated to half in a rotary evaporator. The precipitated crude product is then recrystallized from a mixture of methylene chloride and petrol ether (volume ratio 1:1) and then dried for 48 hours under nitrogen at 40° C./10 mbar in a vacuum drying cabinet.

| Characterization: | |
|---|---|
| Mass spectrum: | molecular peak at 442 |
| Elemental analysis: | |
| Theoretical value (in %): | C: 40.7   H: 1.1   N: 6.3 |
| Found (in %): | C: 40.7   H: 1.0   N: 6.3 |

EXAMPLE 10

Preparation of 1-(3-hydroxy-4-nitro-2,5,6-trifluorophenoxy)-3-(prop-2-enyloxy)-4-nitro-2,5,6-trifluorobenzene

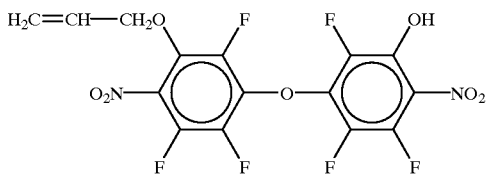

44.2 g of 1-(4-nitro-2,3,5,6-tetrafluorophenoxy)-3-(prop-2-enyloxy)-4-nitro-2,5,6-trifluorobenzene prepared as described in Example 9 (0.1 mol) are dissolved in a mixture of 200 ml of dimethyl sulfoxide and 30 ml of water in a three-neck flask fitted with reflux condenser and stirrer. 15 g of potassium carbonate (0.11 mol) and 10 g of potassium hydrogen carbonate (0.1 mol) are added in portions to the solution, and the mixture is then stirred at 80° C. for 24 hours. The reaction solution is then filtered via a fluted filter, and the crude product is extracted by shaking with 200 ml of ethyl acetate and 400 ml of water. The organic phase is washed three times with water, dried over sodium sulfate and evaporated to half in a rotary evaporator. The precipitated reaction product is then recrystallized from a mixture of methylene chloride and petrol ether (volume ratio 1:1) and then dried for 48 hours under nitrogen at 40° C./10 mbar in a vacuum drying cabinet.

| Characterization: | |
|---|---|
| Mass spectrum: | molecular peak at 440 |
| Elemental analysis: | |
| Theoretical value (in %): | C: 40.9   H: 1.4   N: 6.4 |
| Found (in %): | C: 40.9   H: 1.4   N: 6.3 |

EXAMPLE 11

Preparation of bis(3-hydroxy-4-amino-2,5,6-trifluorophenyl) ether

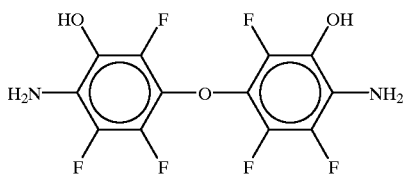

44 g of 1-(3-hydroxy-4-nitro-2,5,6-trifluorophenoxy)-3-(prop-2-enyloxy)-4-nitro-2,5,6-tri-fluorobenzene prepared as described in Example 10 (0.1 mol) are dissolved in 400 ml of a mixture of tetrahydrofuran and ethyl acetate (volume ratio 1:1), and 4.4 g of Pd/C (palladium/carbon) are added to the solution. The solution is then stirred vigorously for 6 hours at room temperature in an autoclave in order to remove the allyl protecting group. Hydrogen is then passed in, and the mixture is hydrogenated at a pressure of 1 bar; after 3 days, the reaction is terminated. The yellow solution is evaporated to half in a rotary evaporator and left to stand at room temperature overnight, during which the reaction product precipitates in crystalline form. The reaction product is then separated off and dried for 48 hours under nitrogen at 40° C./10 mbar in a vacuum drying cabinet.

Characterization:
  Mass spectrum: molecular peak at 340
  Elemental analysis: Theoretical value (in %) : C: 42.4 H: 1.8 N: 8.2. Found (in %) : C: 42.4 H: 1.8 N: 8.2.

EXAMPLE 12

Preparation of 1-(4-nitro-2,3,5,6-tetrafluorophenoxy)-3-benzyloxy-4-nitrobenzene

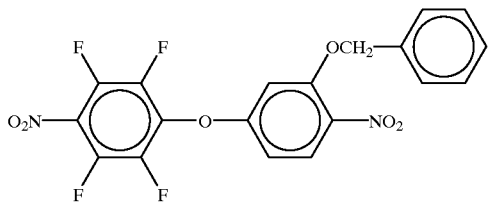

24.5 g of 2-benzyloxy-4-hydroxynitrobenzene (0.1 mol) and 21.3 g of pentafluoronitrobenzene (0.1 mol) are dissolved in 300 ml of γ-butyrolactone in a three-neck flask fitted with stirrer. 30 g of potassium carbonate (0.22 mol) are then added in portions, and the mixture is stirred at room temperature for 24 hours. The reaction solution is then filtered via a fluted filter, and the crude product is extracted by shaking with 200 ml of ethyl acetate and 300 ml of water. The organic phase is washed three times with water, dried over sodium sulfate and evaporated to half in a rotary evaporator. The precipitated crude product is then recrystallized from a mixture of methylene chloride and petrol ether (volume ratio 1:1) and then dried for 48 hours under nitrogen at 40° C./10 mbar in a vacuum drying cabinet.
Characterization:
Mass spectrum: molecular peak at 438
  Elemental analysis: Theoretical value (in %) : C: 52.1 H: 2.3 N: 6.4. Found (in %) : C: 52.1 H: 2.2 N: 6.5.

EXAMPLE 13

Preparation of 1-(3-hydroxy-4-nitro-2,5,6-trifluorophenoxy)-3-benzyloxy-4-nitrobenzene

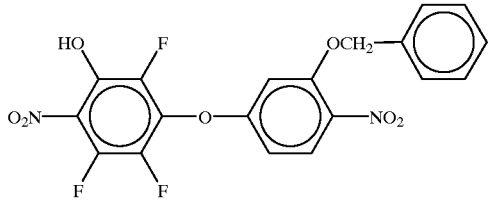

43.8 g of 1-(4-nitro-2,3,5,6-tetrafluorophenoxy)-3-benzyloxy-4-nitrobenzene prepared as described in Example 12 (0.1 mol) are dissolved in a mixture of 200 ml of dimethyl sulfoxide and 30 ml of water in a three-neck flask fitted with reflux condenser and stirrer. 15 g of potassium carbonate (0.11 mol) and 10 g of potassium hydrogen carbonate (0.1 mol) are added in portions to the solution, and the mixture is then stirred at 80° C. for 24 hours. The reaction solution is then filtered via a fluted filter, and the crude product is extracted by shaking with 200 ml of ethyl acetate and 400 ml of water. The organic phase is washed three times with water, dried over sodium sulfate and evaporated to half in a rotary evaporator. The precipitated reaction product is then recrystallized from a mixture of methylene chloride and petrol ether (volume ratio 1:1) and then dried for 48 hours under nitrogen at 40° C./10 mbar in a vacuum drying cabinet.

Characterization:
Mass spectrum: molecular peak at 436
Elemental analysis: Theoretical value (in %) : C: 52.3 H: 2.5 N: 6.4. Found (in %) : C: 52.3 H: 2.4 N: 6.4.

EXAMPLE 14

Preparation of 3-(3-hydroxy-4-amino-2,5,6-trifluorophenoxy)-6-aminophenol

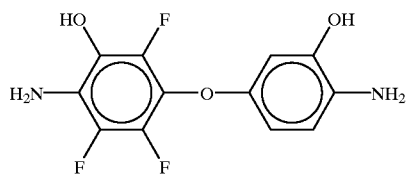

43.6 g of 1-(3-hydroxy-4-nitro-2,5,6-trifluorophenoxy)-3-benzyloxy-4-nitrobenzene prepared as described in Example 13 (0.1 mol) are dissolved in 400 ml of a mixture of tetrahydrofuran and ethyl acetate (volume ratio 1:1), and 4.4 g of Pd/C (palladium/carbon) are added to the solution. The mixture is then hydrogenated at room temperature in an autoclave with vigorous stirring using hydrogen at a pressure of 1 bar; after 3 days, the reaction is terminated. The yellow solution is evaporated to half in a rotary evaporator an left to stand at room temperature overnight, during which the reaction product precipitates in crystalline form. The reaction product is then separated off and dried for 48 hours under nitrogen at, 40° C./10 mbar in a vacuum drying cabinet.

Characterization:
Mass spectrum: molecular peak at 286
Elemental analysis: Theoretical value (in %) : C: 50.4 H: 3.2 N: 9.8. Found (in %) : C: 50.4 H: 3.2 N: 9.8

We claim:
1. An o-nitrophenol or o-nitrothiophenol derivative of the structure

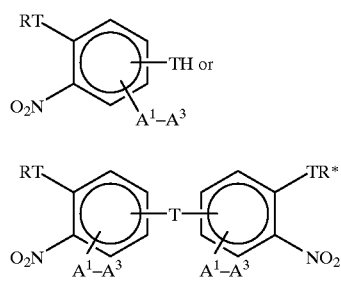

in which:
each of $A^1$ to $A^3$ is a ring substituent independently selected from H, F, $CH_3$, $CH_2CH_3$, $CF_3$, $CF_2CF_3$, $OCH_3$, $OCF_3$, $OCH_2CH_3$ or $OCF_2CF_3$;
each T=O only or each T=S only;
R=alkyl, alkoxyalkyl, alkenyl, alkoxyalkenyl, alkynyl or alkoxyalkynyl, each having a maximum of 6 carbon atoms, phenyl, $C_6H_5COCH_2$ or benzyl, and benzylalkyl, benzylalkenyl, benzyloxyalkyl, benzyloxyalkenyl, benzylalkoxyalkyl or benzylalkoxyalkenyl, each having a maximum of four aliphatic carbon atoms;
R*=H or R;
provided that, in the o-nitrophenol derivative (1), when R is allyl or benzyl the TH group is in the m-position to the TR group and provided that in the o-nitrophenol derivative (1) R is not alkyl; and provided further that on each ring in the o-nitrophenol derivative (2) not more than one of the ring substituents $A^1$ to $A^3$ can be $OCH_3$.

2. An o-nitrophenol or o-nitrothiophenol derivative of the structure

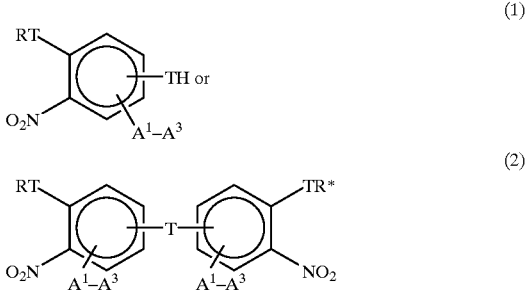

in which:
each of $A^1$ to $A^3$ is a ring substituent independently selected from H, F, $CH_3$, $CH_2CH_3$, $CF_3$, $CF_2CF_3$, $OCH_3$, $OCF_3$, $OCH_2CH_3$ or $OCF_2CF_3$;
T=O;
R is a benzyl group [.], and
R*=H or R;
provided that, in the o-nitrophenol derivative (1), the TH croup is in the m-position to the TR group; and provided further that on each rind in the o-nitrophenol derivative (2) not more than one of the ring substituents $A^1$ to $A^3$ can be $OCH_3$.

3. A compound of claim 1 in which each of $A^1$ to $A^3$ is hydrogen.

4. An o-nitrophenol or o-nitrothiophenol derivative of the structure

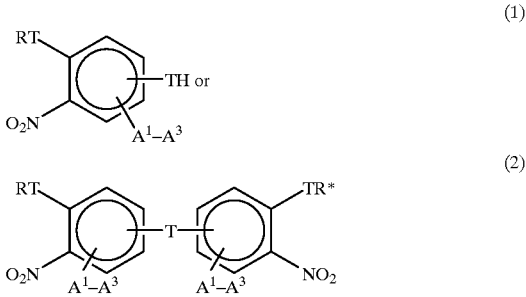

in which:
each of $A^1$ to $A^3$ is fluorine;
each T=O only or each T=S only;
R=alkyl, alkoxyalkyl, alkenyl, alkoxyalkenyl, alkynyl or alkoxyalkynyl, each having a maximum of 6 carbon atoms, phenyl, $C_6H_5COCH_2$ or benzyl, and benzylalkyl, benzylalkenyl, benzyloxyalkyl, benzyloxyalkenyl, benzylalkoxyalkyl or benzylalkoxyalkenyl, each having a maximum of four aliphatic carbon atoms;

R*=H or R;

provided that, in the o-nitrophenol derivative (1), when R is allyl or benzyl the TH group is in the m-position to the TR group and provided that in the o-nitrophenol derivative (1) R is not alkyl.

5. An o-nitrophenol or o-nitrothiophenol derivative having structure (2)

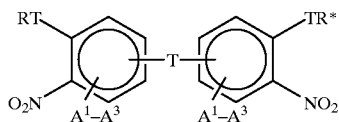
(2)

in which:

each of $A^1$ to $A^3$ in one ring is hydrogen and each of $A^1$ to $A^3$ in the other ring is fluorine;

each T=O only or each T=S only;

R=alkyl, alkoxyalkyl, alkenyl, alkoxyalkenyl, alkynyl or alkoxyalkynyl, each having a maximum of 6 carbon atoms, phenyl, $C_6H_5COCH_2$ or benzyl, and benzylalkyl, benzylalkenyl, benzyloxyalkyl, benzyloxyalkenyl, benzylalkoxyalkyl or benzylalkoxyalkenyl, each having a maximum of four aliphatic carbon atoms; and R*=H or R.

6. A compound of claim 2 having the structure

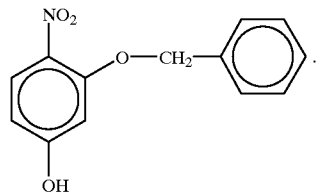

7. A compound of claim 4 having the structure

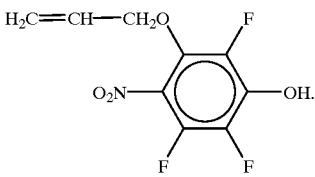

8. A compound of claim 2 having the structure

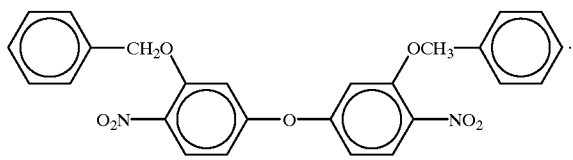

9. A compound of claim 4 having the structure

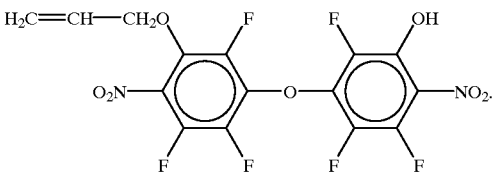

10. A compound of claim 1 having the structure

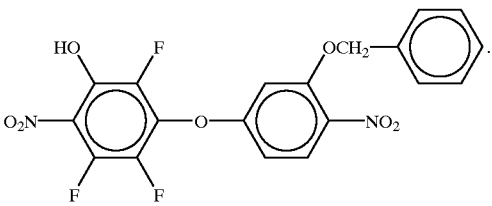

11. A compound of claim 1 in which T is oxygen.
12. A compound of claim 1 in which R is an allyl group.
13. A compound of claim 1 in which R is a benzyl group.

* * * * *